(12) United States Patent
Teague et al.

(10) Patent No.: US 6,569,150 B2
(45) Date of Patent: May 27, 2003

(54) REINFORCED RETENTION STRUCTURES

(75) Inventors: James A. Teague, Spencer, IN (US); Benjamin J. Bottcher, Franklin, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 21 days.

(21) Appl. No.: 09/829,705

(22) Filed: Apr. 10, 2001

(65) Prior Publication Data

US 2001/0047164 A1 Nov. 29, 2001

Related U.S. Application Data

(60) Provisional application No. 60/195,995, filed on Apr. 11, 2000.

(51) Int. Cl.[7] .................... A61M 25/00; A61M 27/00
(52) U.S. Cl. .................. 604/524; 604/526; 604/527; 604/104
(58) Field of Search .................. 604/523–230, 604/531–544, 48, 264, 902, 96.01, 104

(56) References Cited

U.S. PATENT DOCUMENTS

| | | | |
|---|---|---|---|
| 3,592,197 A | 7/1971 | Cohen | |
| 4,212,304 A | 7/1980 | Finney | 128/349 |
| 4,307,723 A | 12/1981 | Finney | 128/349 |
| 4,503,569 A | 3/1985 | Dotter | 3/1.4 |
| 4,820,262 A | 4/1989 | Finney | |
| 4,874,360 A | 10/1989 | Goldberg et al. | 604/8 |
| 4,931,037 A | 6/1990 | Wetterman | 604/8 |
| 4,985,022 A | 1/1991 | Fearnot et al. | 604/282 |
| 5,069,226 A * | 12/1991 | Yamauchi et al. | 128/772 |
| 5,112,310 A * | 5/1992 | Grobe | 604/175 |
| 5,147,370 A | 9/1992 | McNamara et al. | 606/108 |
| 5,231,989 A * | 8/1993 | Middleman et al. | 128/657 |
| 5,282,860 A | 2/1994 | Matsuno et al. | |
| 5,380,304 A * | 1/1995 | Parker | 604/282 |
| 5,466,242 A | 11/1995 | Mori | 606/198 |
| 5,472,435 A | 12/1995 | Sutton | 604/282 |
| 5,596,996 A * | 1/1997 | Johanson et al. | 128/772 |
| 5,597,378 A | 1/1997 | Jervis | 606/78 |
| 5,599,291 A | 2/1997 | Balbierz et al. | 604/8 |

(List continued on next page.)

FOREIGN PATENT DOCUMENTS

| | | |
|---|---|---|
| EP | 0 588 959 B1 | 3/1994 |
| EP | 0963764 A1 | 12/1999 |
| WO | WO 93/15785 | 8/1993 |
| WO | WO 93/15872 | 8/1993 |
| WO | WO 97/37717 | 10/1997 |

OTHER PUBLICATIONS

PCT International Search Report, PCT/US01/11678, 5 pgs.

Primary Examiner—Timothy L. Maust
Assistant Examiner—Anuradha Ramana
(74) Attorney, Agent, or Firm—Testa, Hurwitz & Thibeault, LLP

(57) ABSTRACT

A medical device includes an elongated member and a reinforced retention structure. The device can be used for draining substances from organs or abscessed areas within a body of a patient. The elongated member is made of a flexible material. The reinforced retention structure extends from or is formed integrally with the elongated member and comprises an elastic member and the flexible material. The reinforced retention structure provides retention strength while providing flexibility and patient comfort. The use of the reinforced retention structure also provides increased stability to the device within the patient's body and combats migration and/or expulsion of the device. The nature of the reinforcement in the retention structure may extend into the elongated member, which allows for larger drainage openings in the device and increases the radiopacity of the device.

60 Claims, 10 Drawing Sheets

U.S. PATENT DOCUMENTS

| | | | |
|---|---|---|---|
| 5,704,926 A | | 1/1998 | Sutton .................. 604/282 |
| 5,782,916 A | | 7/1998 | Pintauro et al. .......... 623/12 |
| 5,792,124 A | * | 8/1998 | Horrigan et al. ......... 604/282 |
| 5,858,009 A | | 1/1999 | Jonkman ................ 604/264 |
| 5,885,258 A | * | 3/1999 | Sachdeva et al. ......... 604/281 |
| 5,928,208 A | * | 7/1999 | Chu et al. ............... 604/280 |
| 5,928,217 A | | 7/1999 | Mikus et al. ............ 604/530 |
| 5,935,107 A | | 8/1999 | Taylor et al. |
| 5,964,744 A | | 10/1999 | Balbierz et al. .......... 604/530 |
| 5,976,120 A | | 11/1999 | Chow et al. ............. 604/525 |
| 5,989,288 A | | 11/1999 | Pintauro et al. ........... 623/12 |
| 6,013,102 A | | 1/2000 | Pintauro et al. ........... 623/12 |
| 6,063,119 A | | 5/2000 | Pintauro et al. ........... 623/12 |
| 6,159,177 A | | 12/2000 | Amos, Jr. et al. ......... 604/95 |
| 6,165,163 A | * | 12/2000 | Chien et al. ............. 604/523 |
| 6,183,506 B1 | | 2/2001 | Penn et al. .............. 623/1.15 |
| 6,183,520 B1 | | 2/2001 | Pintauro et al. ........ 623/23.64 |
| 6,213,996 B1 | * | 4/2001 | Jepson et al. ............ 604/533 |
| 6,221,059 B1 | * | 4/2001 | Chiang et al. ........... 604/264 |
| 6,240,322 B1 | * | 5/2001 | Peterfeso et al. ......... 607/126 |
| 6,254,570 B1 | * | 7/2001 | Rutner et al. ......... 604/101.02 |
| 6,312,454 B1 | * | 11/2001 | Stockel et al. ............. 623/1 |
| 6,355,056 B1 | * | 3/2002 | Pinheiro ................ 623/1.13 |
| 6,436,056 B1 | * | 8/2002 | Wang et al. ............. 600/585 |

* cited by examiner

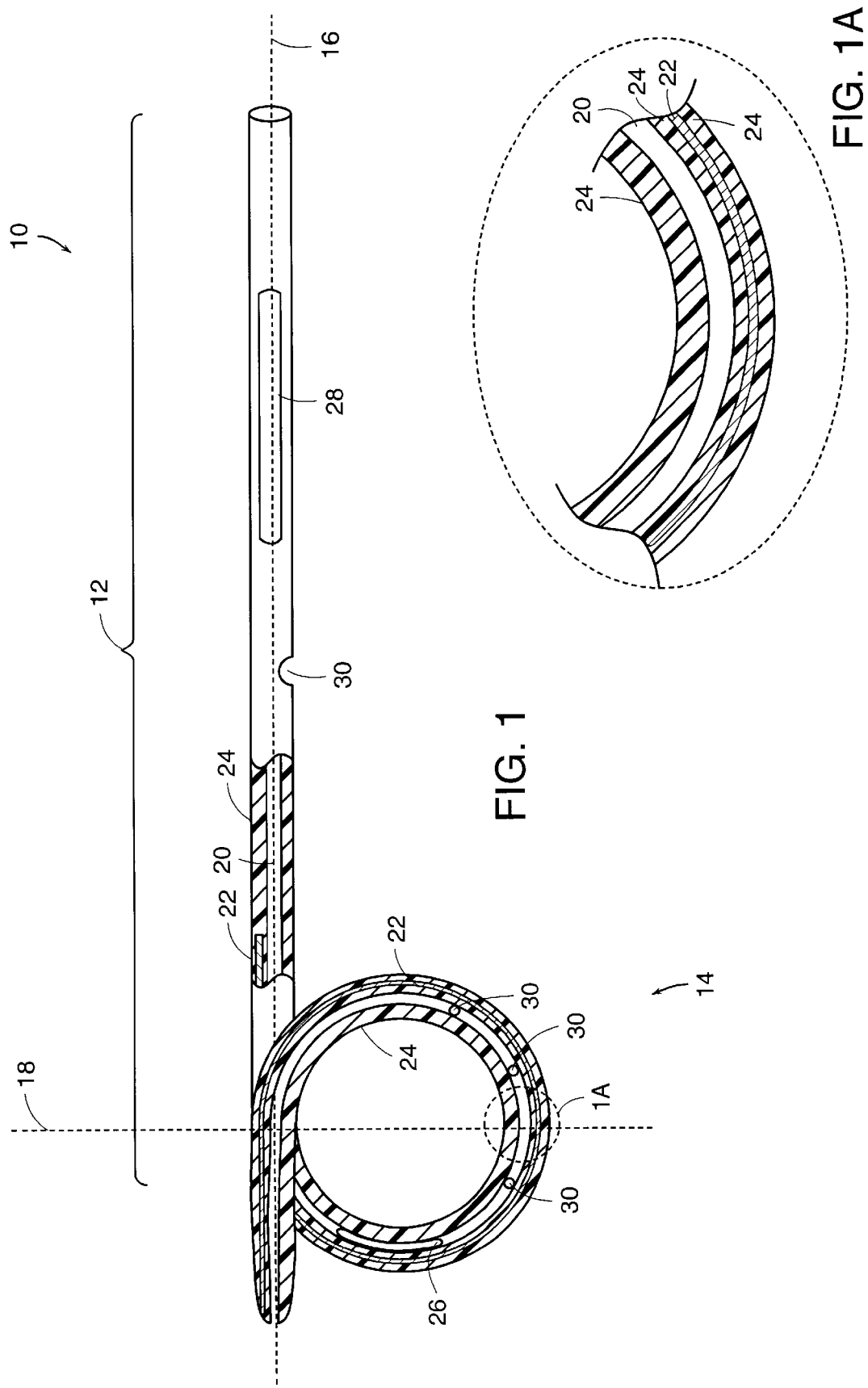

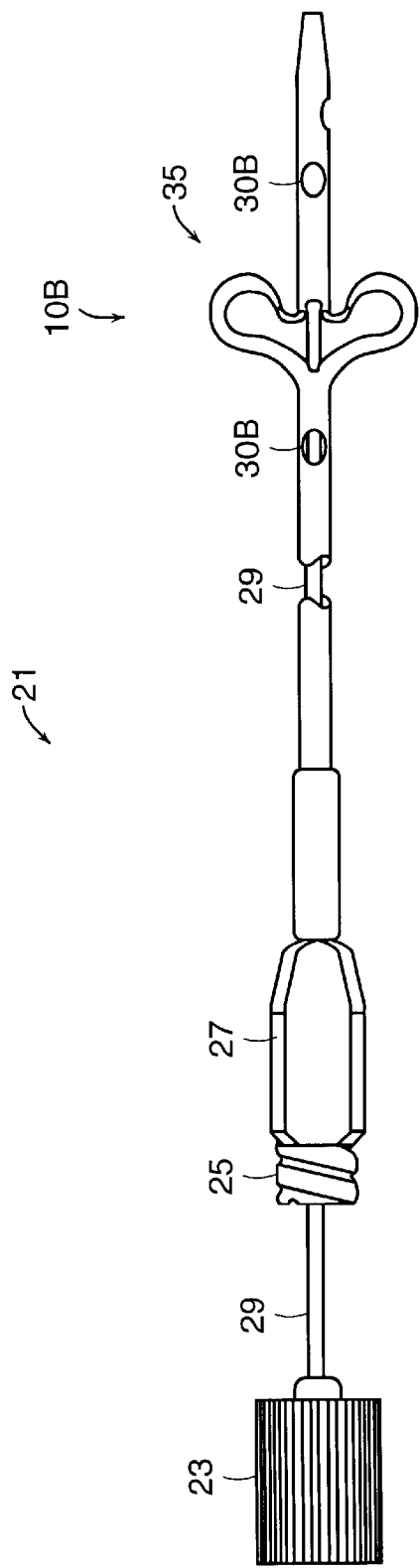
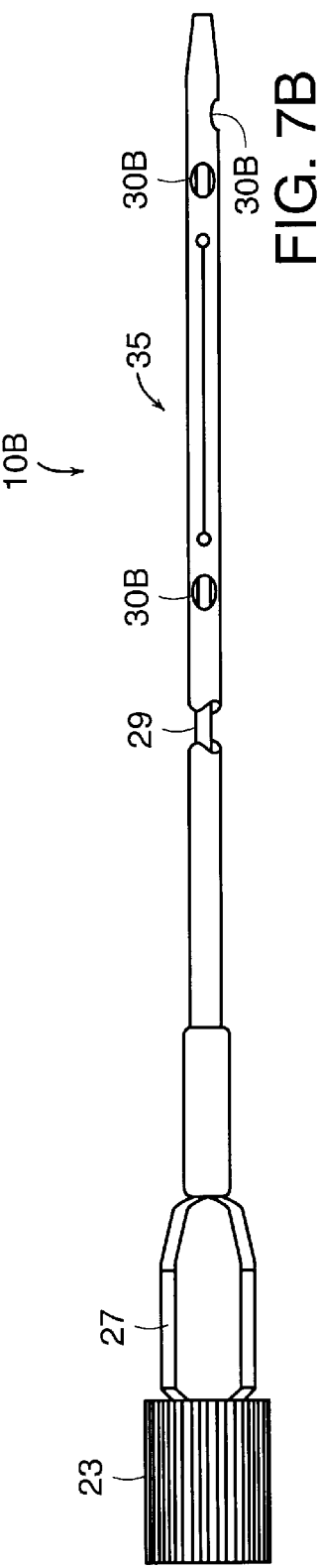
FIG. 7A
FIG. 7B

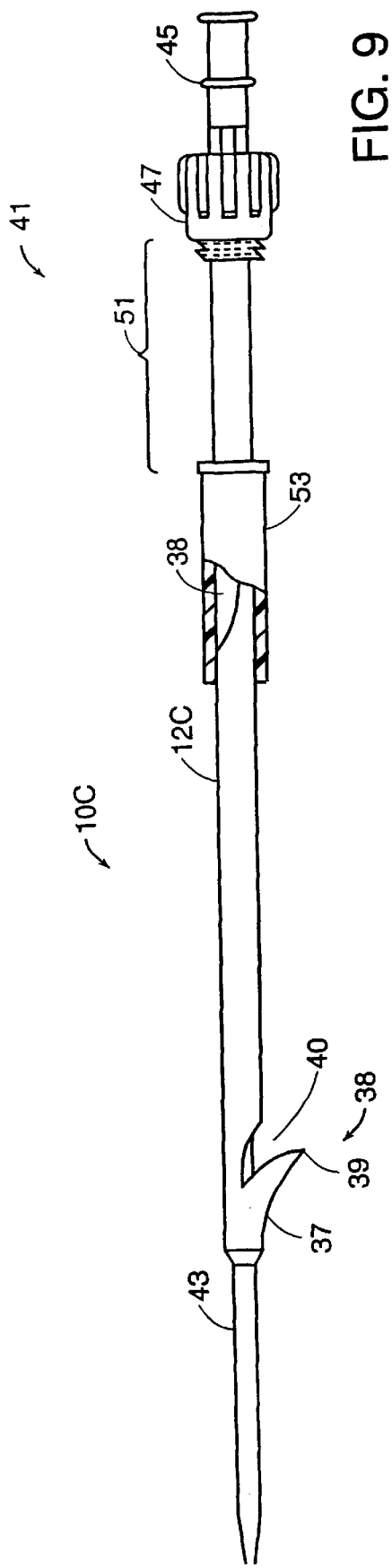
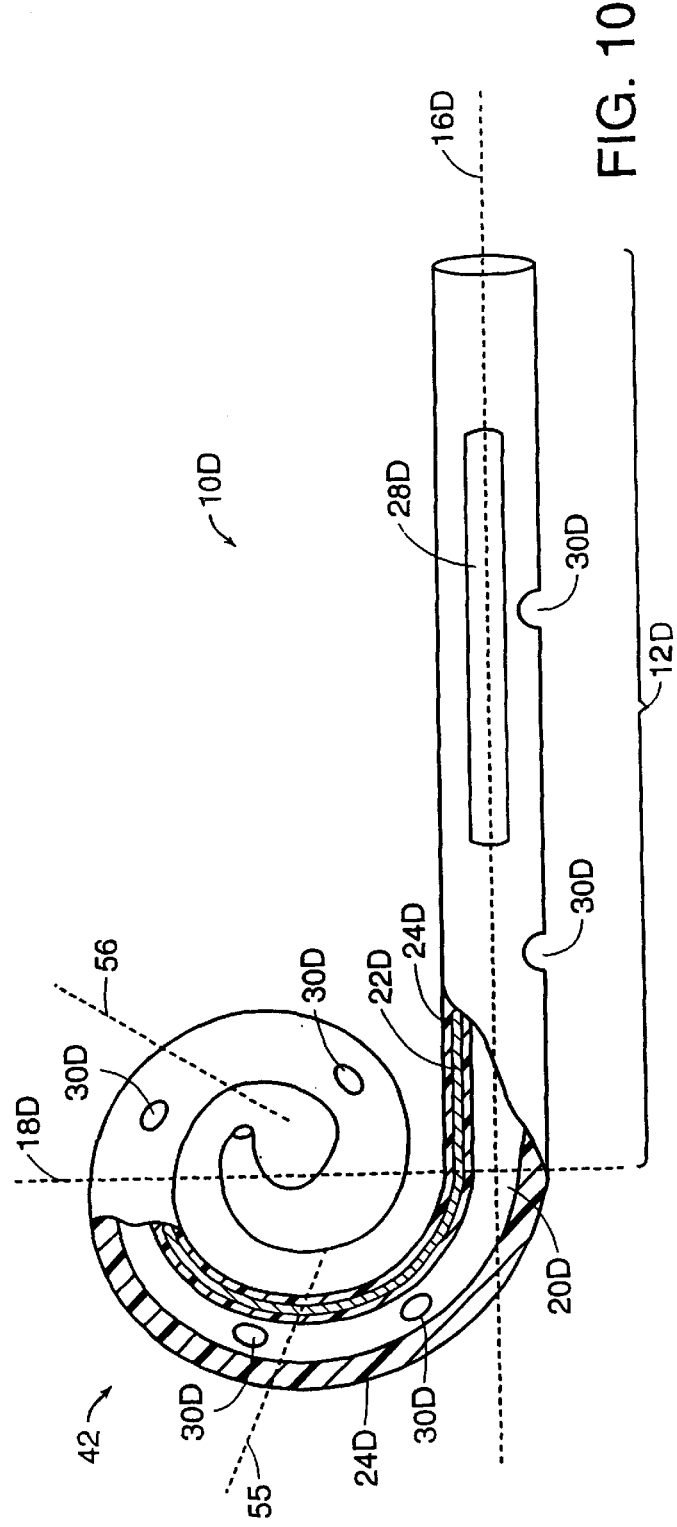
FIG. 9
FIG. 10

REINFORCED RETENTION STRUCTURES

RELATED APPLICATIONS

This application claims the benefit of U.S. Provisional Application No. 60/195,995, filed Apr. 11, 2000.

TECHNICAL FIELD

This invention generally relates to medical devices, such as drainage stents and catheters.

BACKGROUND INFORMATION

Medical devices used for draining fluids from body cavities are generally made of plastic tubing. The tubing is often pre-formed on one or both of its ends to a geometry designed to maintain or anchor the device in position within the body. Medical devices of this type are commonly placed through a ureteroscope, laprascope, or endoscope and into lumens and/or body orifices. In the case of abscess catheters, placement generally occurs percutaneously through a puncture of the external dermis and musculature. In most cases, however, a guidewire is first passed through the orifice or puncture to the desired drainage site, around or through obstacles if required. The medical device is then placed over the guidewire through a lumen running the full length of the device. This straightens the anchoring geometry to ease and allow insertion. After insertion, the guidewire is pulled out through the device's proximal end. Once the guidewire is removed from the body, the anchoring geometry assumes its natural, pre-formed shape to retain the device in position within the body of the patient.

Some medical devices use coils or pigtails as anchors in an open area of the anatomy, such as the renal pelvis of a kidney or abscessed area within a body cavity. These types of anchors allow the device (such as a ureteral drainage stent) to maintain its position within the body by blocking its migration through thinner tract openings. Another type of anchoring mechanism is commonly known as a malecot. Some other devices, such as biliary stents, use one or more barbs (formed, for example by partially skiving a tube in a longitudinal direction). Some biliary stents use barbs for retention in the biliary tract.

SUMMARY OF THE INVENTION

Known anchoring mechanisms used with medical devices can fail. For example, internal forces from involuntary bodily functions (such as peristalsis and other secretory forces, as well as patient movement) can force the device out of its intended position within the body. In addition, doctors typically recommend catheter and stent anchoring or retention structures fabricated from softer materials to enhance patient comfort. These softer materials generally have lower retention strengths as compared to more rigid materials. Also, the lower strengths of these softer materials limits the size of holes that can be formed in the medical device to help drain fluid from the body of a patient.

The present invention provides significantly increased strength to retention structures while also maintaining patient comfort. With the invention, softer materials can be used to maximize patient comfort, and reinforcement of these soft materials affords greater retention properties. Examples of devices that can include retention structures according to the present invention include, but are not limited to, a drainage catheter, a ureteral stent, a urethral stent, a biliary stent, and a prostatic stent.

In general, one aspect of the present invention relates to a medical device comprising an elongated member and a reinforced retention structure. The elongated member comprises a flexible material and defines a lumen extending therethrough. The reinforced retention structure extends from the elongated member and comprises an elastic member and the flexible material.

The elastic member may be embedded within the flexible material, or bound to a surface of the retention structure such as the inner or outer wall of the retention structure. The retention structure may extend from the distal or proximal portions of the device, lie between the distal and proximal portions in a middle portion, or exist in or on two or more portions of the device.

As used herein, "distal portion" refers to the portion of the medical device furthest away from the medical operator inserting the device within the open or abscessed area of the anatomy, such as the portion in and/or near the kidney. "Proximal portion" refers to the opposite portion of the device closest to the medical operator, such as the portion in and/or near the urinary bladder. "Middle portion" refers to the portion of the medical device that lies between the distal and proximal portions.

In some embodiments, at least one large drain hole slot is formed through the wall of the retention structure. The use of the elastic member in the retention structure eliminates the risk that the retention structure will collapse on itself because of the size of the drain holes. Alternatively or additionally, the elastic member may extend into the elongated member. Because of the stability provided by this configuration, a large drain hole slot may be cut into the elongated member in place of typical smaller drain hole configurations. Also, the elastic member increases the radiopacity of at least the retention structure, thereby enhancing the locatability of the device (or at least the retention structure) using flouroscopy.

The extension of the elastic member into the elongated member also enhances pushability of the device during insertion into a body of a patient. The elastic member prevents the device from kinking as it moves within the body. In one embodiment, the elastic member may be removable from the elongated member after insertion. Under this construction, two separate elastic members reside in the retention structure and the elongated member. The length of the elastic member disposed in the elongated member exceeds the length of the device. After insertion of the device into the body of the patient, the operator proximally pulls the elastic member residing in the elongated member from the patient's body. The elastic member residing in the retention structure remains in place.

The shape of the retention structure and its positioning with respect to the elongated member can vary in different embodiments according to the invention. The retention structure may be formed integrally with the elongated member or it may be affixed to the elongated member. A retention structure may be located anywhere along the length of the elongated member. Also, two or more retention structures may be disposed along the length of the elongated member.

In one embodiment, a elastic member is pre-formed to a curved shape and disposed within the wall of a plastic tubing. The curved shape may be a retention structure with a single turn, a retention structure with two or more turns, or simply a J curl. In another embodiment, a plurality of lengths of a pre-formed elastic material can be positioned longitudinally in the wall of a piece of tubing surrounding a central lumen. Portions of the tubing can then be cut longitudinally in between the superelastic pieces to form the arms of a malecot. In another embodiment, a dual-lumen tube is partially skived at one end into a barbed configuration. A preformed curved piece of elastic material is secured in the skived portion for added strength.

In other embodiments, one or more elastic rings radially protruding from the elongated member and containing a reinforcing superelastic ring and a flexible material may be formed or disposed along the elongated member as a retention structure. By varying the size of the rings, the device can accommodate body cavities of different shapes and sizes and work in maintaining the lumen of the tube wide open. The elastic ring or rings may be constructed from a variety of flexible materials, such as elastomeric compounds. Materials like these combine rigidity and the softness necessary for patient stability and comfort.

In all of the above-described embodiments, a plurality of drain holes may be cut into the elongated member and/or retention structure to maximize drainage. Alternatively or additionally, large drain hole slots can be cut into the elongated member and/or retention structure depending on the placement of the elastic member.

In other aspects, the invention involves methods of placing medical devices, such as the devices previously described. A method of placing a medical device of the invention into the body of a patient comprises providing the device, collapsing the retention structure and inserting the device into a patient's body to release the retention structure, and thereby deploy the medical device in the body.

In another aspect, the invention involves methods of making medical devices of the present invention. A method of making such a device comprises extruding an elongated member made of a flexible material and incorporating a pre-formed elastic member to the flexible material by embedding the elastic member within the flexible material or by binding the elastic member to a surface or groove of the flexible material to form a reinforced retention structure.

The foregoing and other objects, aspects, features, and advantages of the invention will become more apparent from the following description, drawings, and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a schematic side view of one embodiment of the medical device of the invention with an elongated member and a single loop retention structure.

FIG. 1A is an enlarged cross sectional view of a cut-out portion of the single loop retention structure of FIG. 1.

FIGS. 7A–B show two side views of an insertion catheter with stylet for inserting embodiments of a medical device of the invention into a body of a patient with the retention structure deployed (A) and collapsed (B).

FIG. 9 shows a longitudinal view of an insertion catheter with stylet and cannula for inserting an embodiment of the medical device of the invention into a body of a patient.

FIG. 10 is a schematic longitudinal view in partial longitudinal cross-section of one embodiment of the medical device of the invention with an elongated member and an inward spiral coil.

DESCRIPTION

Figure 2A:
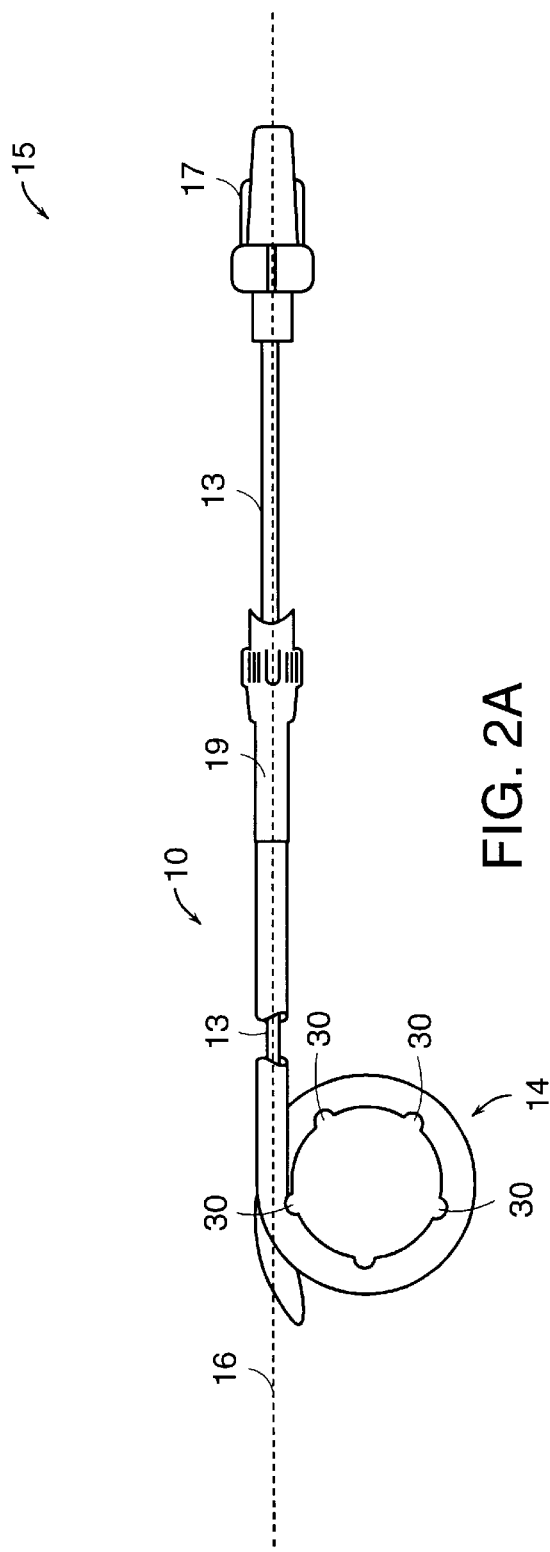
FIGS. 2A–B show two side views of an insertion catheter with stylet for collapsing a single loop retention structure and inserting the catheter into a body of a patient with the retention structure deployed (A) and collapsed (B).

Medical devices of the present invention are generally constructed of an elongated member and a reinforced retention structure. The elongated member includes a flexible material and the reinforced retention structure includes the same or a different flexible material with an elastic member embedded within or bound to a surface or groove of the flexible material. Preferred materials for the flexible material include, but are not limited to plastic, silicone, TEFLON®, and other PTFE polymers, polyurethane polymers and the like. These materials may also be provided with radiopaque portions to assist in the implantation of the devices in a body of a patient under fluoroscopic monitoring.

The elongated member may be tubular or conical or a combination of both. Generally, the elongated member comprises a lumen extending through the entire length of the elongated member to provide drainage of fluid from a body cavity. Alternatively or additionally, drainage may be provided or enhanced by grooves located on the external surface of the retention structure and/or elongated member.

The reinforced retention structure is designed to anchor the medical device in place notwithstanding certain forces such as internal forces from involuntary bodily functions such as peristalsis and other secretory forces, or patient movement. The reinforced retention structure may be formed as an extension of the elongated member. Under this construction, an elongated member is molded into a predetermined shape to form a reinforced retention structure such that it can extend from the elongated member. Alternatively, a reinforced retention structure may be fixedly mounted to the elongated member in that both the elongated member and retention structures are pre-formed and thereafter attached to one another. The reinforced retention structure may adopt any geometry that protrudes laterally or radially from the elongated member to provide adequate anchoring.

Examples of retention structure geometry include, but are not limited to, a retention coil including one turn, a retention coil including two or more turns, a J curl, an inward spiral coil, a barb, a malecot, and a protruding ring. The retention structure and/or the elongated member itself can have a number of drainage holes disposed along its length. The holes provide drainage areas to allow fluids to drain into the lumen of the elongated member. Alternatively or additionally, a large drain hole slot (FIG. 12b) may be cut into the retention structure and/or the elongated member to further facilitate drainage.

Retention structures according to the invention may be reinforced by a segment made of an elastic member embedded within the flexible material or bound to a surface or groove of the retention structure (such as the inner or outer wall of the retention structure). The elastic member may have a cross-section that can be round, flat, square, crescent or D-shaped. Certain examples of these cross-sectional shapes are illustrated in FIGS. 3A–C and 4A–C.

The elastic member may be fabricated from a material having "superelastic" properties. Materials with superelastic properties, make it possible to configure a segment into a particular advantageous shape of a retention structure, such as a pigtail, a malecot arm, a coil, a barb or a ring and then modify reversibly the geometry of the retention structure by straightening the retention structure through use of guidewires, outer sheaths and the like for easy implantation in the body. For example, the pigtail, malecot, and coil retention structures assume straightened geometries when placed over or within the length of a cannula. After the device is straightened, placement into a body with conventional insertion techniques may occur. After insertion and removal of the straightening device, the elastic member reverts spontaneously to its predetermined configuration thereby regaining its deployed geometry and reforming the retention structure.

The superelastic material may comprise an alloy of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn. Preferably, the superelastic material comprises a nickel and titanium alloy, known commonly as Nitinol available from Memry Corp of Brookfield, Conn. or SMA Inc. of San Jose, Calif. The ratio of nickel and titanium in Nitinol may be varied. Examples include a ratio of about 50% to about 52% nickel by weight or a ratio of about 47% to about 49% nickel by weight. Nitinol has shape retention properties in its superelastic phase.

In other embodiments, the elastic member comprises any suitable material that has sufficient elastic properties to allow for straightening of the retention structure during insertion into the body, but provides desired reinforcement strength to the retention structure during use. Such materials include, for example, stainless steel or suitable polymeric materials.

The elastic member disposed within the retention structure may have a one-dimensional shape, such as a linear wire, a two-dimensional shape, such as a curled wire to form a loop or an inward coil, or a three-dimensional shape, such as a helical coil or a pigtail coil. In two-dimensional embodiments, the wire may be bent along a second axis such that the wire occupies a plane. In three-dimensional embodiments, the wire may be coiled tightly about itself within the retention structure.

An embodiment of a medical device 10 according to the present invention is shown in FIG. 1. The medical device comprises an elongated member 12 and a reinforced retention structure 14. The elongated member may be viewed as extending along a first axis 16. In FIG. 1 the first axis 16 extends in a longitudinal direction. The retention structure 14 extends along the first axis 16 and a second axis 18. As seen in FIG. 1, the second axis 18 extends laterally from the first axis 16. The elongated member 12 defines an internal lumen 20. The internal lumen 20 also extends into and through the retention structure 14.

In FIG. 1, the retention structure 14 is shaped into a coil including a single turn. The retention structure comprises a reinforcing structure made of an elastic member 22 embedded within a flexible material 24. FIG 1A is an enlarged cross sectional view of an portion of the single loop retention structure of FIG. 1, and depicts the elastic member embedded within the flexible material. Alternatively, the reinforcing elastic member 22 may be bound to an inner or outer wall of the flexible material 24. The stability provided by the elastic member 22 to the retention structure 14 allows for a large drain hole slot 26 to be cut into the retention structure 14 alongside the reinforcing material 22. Optionally, the elastic member 22 can extend into the elongated member 12. A large drain hole slot 28 may be cut into a portion of a wall of the elongated member 12 for increased drainage. To facilitate drainage, both the retention structure 14 and/or the elongated member 12 may, alternatively or additionally, incorporate a plurality of drainage holes 30 disposed along their lengths to permit drainage of fluid into the lumen 20.

Figure 2B:
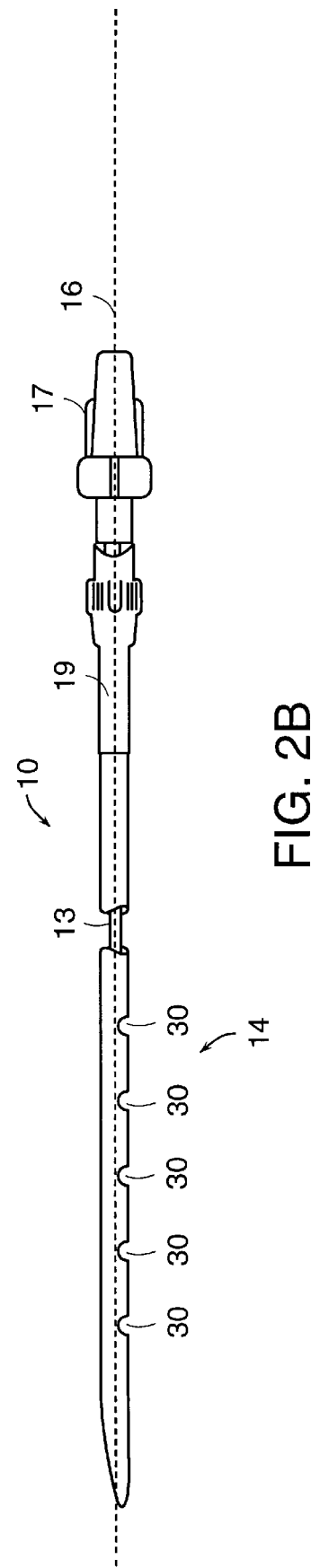

Insertion of the device 10 into a body of a patient can be accomplished by straightening the retention structure 14 with a rigid elongated member along the first axis 16, such as inserting a stylet or guidewire within the lumen 20 or a cannula or sheath over the elongated member, inserting the device 10 with the rigid member into the body and removing the rigid member from the device to deploy the retention structure once the device has been inserted and properly positioned within a body cavity. Removal of the rigid member from the device 10 releases the constraint on the elastic member and allows the retention structure to regain its shape. For example, referring to FIGS. 2A–B, a catheter includes a rigid member 13 connected to a handle 17 manually inserted into the lumen of the device 10. The catheter 15 comprises an adapter 19 for attaching the medical device 10 to the handle 17, another catheter, or a collection bag. When the rigid member 13 extends throughout the entire device 10 as in FIG. 2B, the single coil retention structure 14 is straightened along the longitudinal axis 16. The insertion catheter 15 is then inserted into a body of a patient, and the rigid member 13 is removed from the body proximally. The elastic member allows the retention structure 14 to regain its coiled shape in the body upon removal of the rigid member 13 as in FIG. 2A.

Figure 3A:
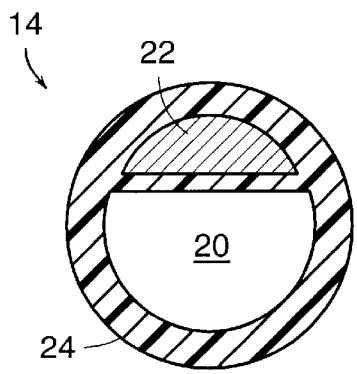
FIGS. 3A–C show transverse cross-sectional views of various embodiments of retention structures of medical devices of the invention.
Figure 3B:
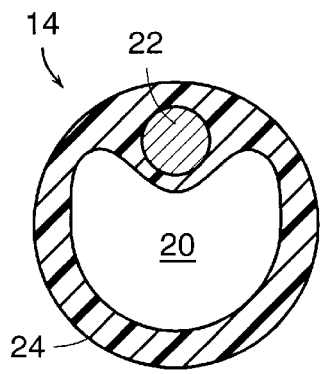
Figure 3C:
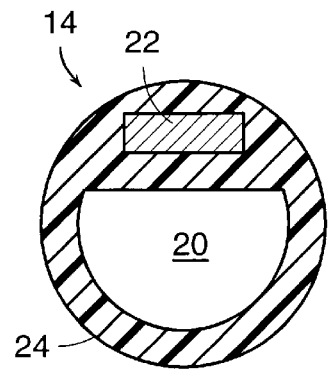

The elastic member may have a variety of shapes and arrangements within the wall of the flexible material 24 forming the retention structure. For example, FIGS. 3A–C represent cross-sectional views of retention structures 14 of the present invention, and show a wire made of a elastic core 22 disposed within the wall of the retention structure 14. This configuration and these shapes may be suitable for coiled reinforced retention structures (e.g. FIGS. 1, 5, and 10) or barbed retention structures (e.g. FIG. 8). In cross-section, the inner lumen 20 is surrounded by the walls of the retention structure 14 with the elastic member 22 embedded within the flexible material 24. The elastic member 22 embedded within the flexible material 24 may be D-shaped as shown in FIG. 3A, round as in FIG. 3B, or flat, rectangular, or ribbonlike as in FIG. 3C. The elastic member may also have more complex shapes such as wires with enlarged or thinner segments along their length, or more intricate shapes such as an arrow head for a barb or the like.

Figure 4A:
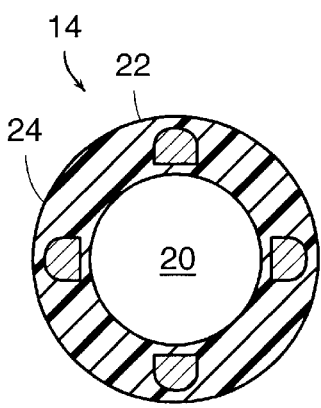
FIGS. 4A–C show additional transverse cross-sectional views of various embodiments of retention structures of medical devices of the invention.
Figure 4B:
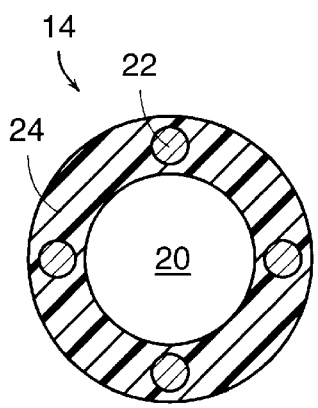
Figure 4C:
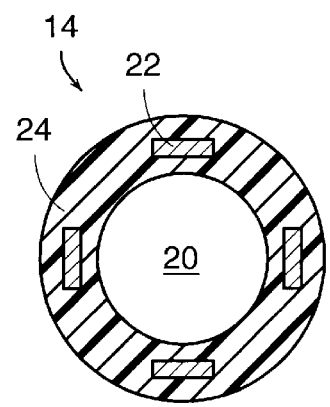

Alternatively, the retention structure may have more than one elastic core disposed at various intervals (regular or irregular) within the wall of the flexible material. For example, FIGS. 4A–C show four superelastic cores 22 having various shapes disposed within the wall of the retention structure 14. In cross-section, within the retention structure 14, an inner lumen 20, is surrounded by the flexible material 24. Elastic member 22 is disposed within the flexible material 24 of the retention structure 14. In the cross-sectional views of the embodiments displayed in FIGS. 4A–C, the elastic member 22 is disposed at four different locations within the flexible material 24. These four locations lie at 0°, 90°, 180°, and 270° angles along the radius of the retention structure 14. The elastic member may, however, lie at any combination of angles along the radius of the retention structure 14. These configurations may be suitable to a coil (e.g. FIGS. 1, 5, and 10) multiple barbs (e.g. FIG. 8) or multiple arms of a malecot retention structure (e.g. FIG. 6). The elastic member 22 within the flexible material 24 may be D-shaped as in FIG. 4A, round as in FIG. 4B, or flat, rectangular, or ribbonlike as in FIG. 4C.

Figure 5:
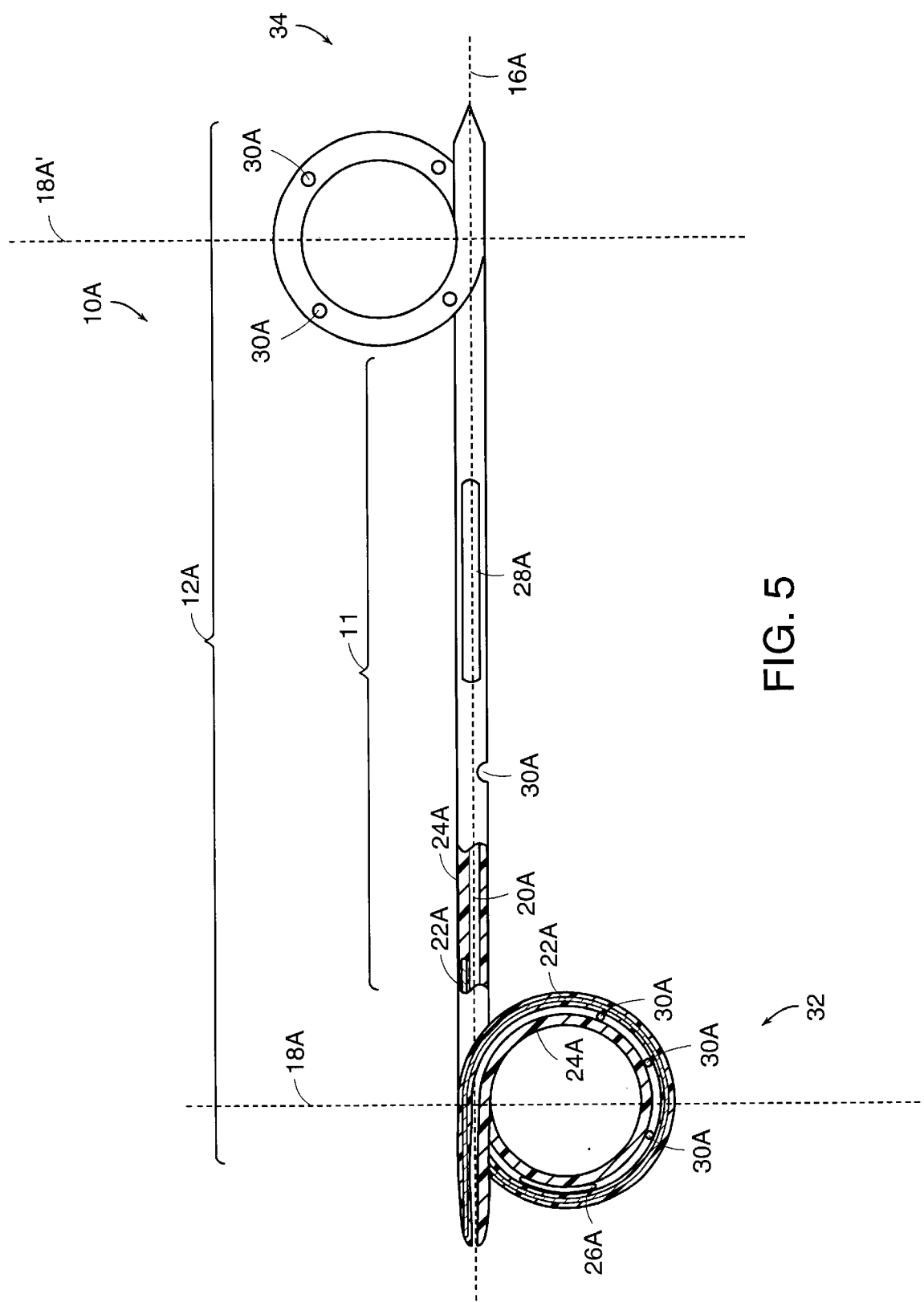
FIG. 5 is a schematic longitudinal view of the medical device of the invention with an elongated member and two retention structures.

Referring now to FIG. 5, another embodiment of a medical device 10A according to the invention is shown. The device 10A is suitable for use as a ureteral stent, and is made of a flexible material forming an elongated member 12A. The elongated member 12A extends along a longitudinal axis 16A and forms two retention structures 32 and 34 at its proximal and distal ends defining a longitudinal portion 11 therebetween. The retention structures extend along lateral axes 18A and 18A' relative to the longitudinal axis 16A. Here, both retention structures 32 and 34 occupy the same plane. But the retention structures 32 and 34 may occupy different planes. The use of dual retention structures provides increased stability to the device within a patient's body and combats migration and/or expulsion of the device 10A. The two or more retention structures 32 and 34 may also be positioned anywhere along the length of the elongated member 12A. The elastic member 22A embedded within the flexible material 24A may be positioned in one or both of these retention structures 32 and 34 and may extend along a short segment of the wall in the longitudinal portion 11.

The enhanced stability provided to the device 10A by the elastic member 22A in the flexible material 24A allows for a large drain hole slot 26A or slots to be cut into the side of one or both of the retention structures 32 and 34. Alternatively or additionally, a large drain hole slot 28A may be cut into the side of the longitudinal portion of the elongated member 12A that contains the extension of the elastic member 22A in the flexible material 24A. A plurality of drain holes 30A may be disposed along the elongated member 12A and/or the retention structures 32 and 34 to permit drainage of fluid into the lumen.

Figure 6:
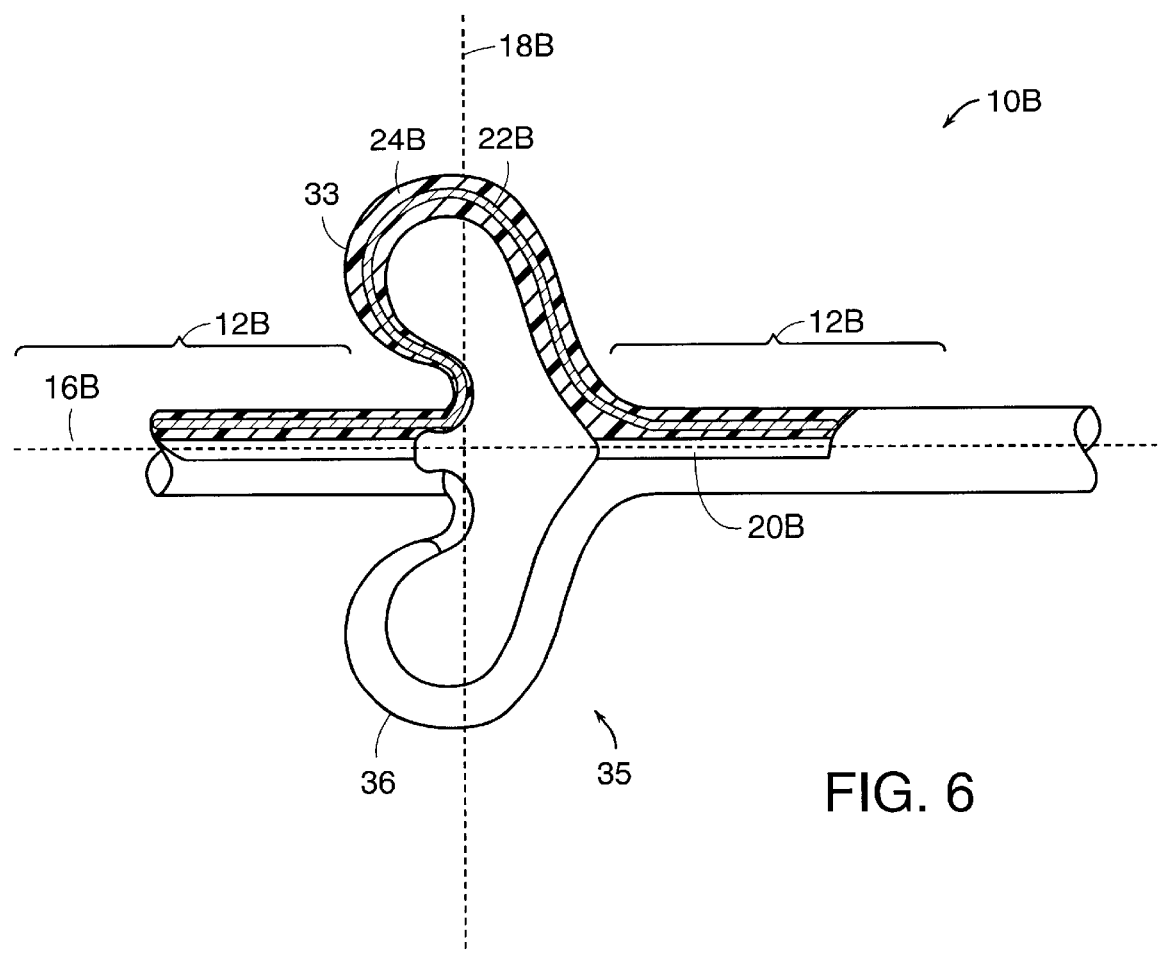
FIG. 6 is a schematic longitudinal view in partial longitudinal cross-section of a portion of an embodiment of the medical device of the invention with an elongated member and a reinforced malecot.

FIG. 6 depicts a retention structure 35, known as a malecot, with two or more laterally bulging arms formed along a portion of a length of an elongated member 12B. The elongated member 12B extends along a longitudinal axis 16B. Two arms 33 and 36 of the retention structure 35 extend along a lateral axis 18B relative to the longitudinal axis 16B. The malecot 35 may also comprise a plurality of collapsible bulging arms including, but not limited to, any number of arms from two arms to eight arms, for example, with three to six arms typical. As with other retention structure constructions, the malecot 35 comprises an elastic member 22B embedded within the flexible material 24B in each of the malecot's arms. In their deployed shape, the arms may have a symmetrical omega (Ω) shape or an omega shape tilted proximally or distally as shown in FIG. 6.

Formation of the malecot 35 can be a multi-step process. A piece of tubing may be first extruded, molded or otherwise shaped into an elongated member 12B to have a central lumen 20B surrounded by a series of smaller outer lumens disposed into the wall of the elongated member 12B and surrounding the lumen 20B. Lengths of elastic material are shaped into curved geometries formed by a sequence of alternating convex and concave curves of varied length and radii that shape the arms of the malecot. These preformed lengths of elastic material 22B are then placed into the outer lumens of the flexible material 24B. The multi-lumen tubing is then cut longitudinally between each of the pieces of elastic material 22B to separate the arms of the malecot from each other.

The elastic member 22B allows the arms of the malecot 35 to protrude laterally from the elongated member 12B in a natural state, and collapse to lie flat along the length of the elongated member 12B for insertion of the device 10B as seen in FIGS. 7A–B. A plurality of drain holes 30B may be disposed along the elongated member 12B of the device 10B to permit drainage of fluid into the lumen. An insertion catheter 21 comprising a rotatable handle 23 having internal threads, a threaded element 25 that interlocks with the rotatable handle 23, a molded hub 27, a rigid member 29, and a malecot in an expanded state is shown in FIG. 7A. To collapse the malecot 35, the device 10B is disposed on the rigid member 29 while holding the molded hub 27 steady. Longitudinal tension exerted on device 10B by opposing tugs exerted on the hub 27 and distal end of the rigid member 29 pulls opposite ends of the device 10B apart and collapses the malecot 35. FIG. 7B shows the malecot 35 in its collapsed state.

After the malecot has been collapsed, the insertion catheter 21 may be directly inserted into a body of a patient. The rigid member 29 is released from the device 10B by rotating the handle 23 to release it from the hub 27. Removal of the rigid member 29 releases tension on the device 10B and allows the elastic member to resume its expanded shape deploying the malecot and securing the device 10B within the body.

Figure 8:
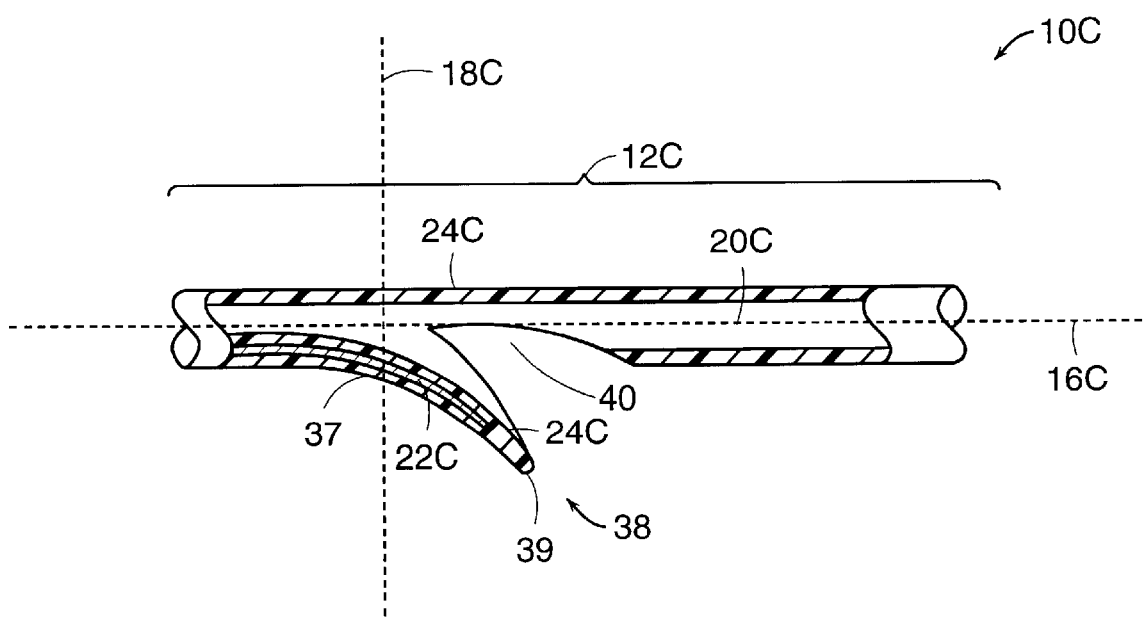
FIG. 8 is a schematic longitudinal view in partial longitudinal cross-section of a portion of an embodiment of the medical device of the invention with an elongated member and a reinforced barb.

FIG. 8 depicts a retention structure 38 as a barb having two ends. One end 37 of the barb is formed integrally with the elongated member 12C. The other end 39 of the barb extends laterally from the elongated member 12C. The elongated member 12C defining a central lumen 20C extends along a longitudinal axis 16C. The retention structure 38 extends along a lateral axis 18C relative to the longitudinal axis 16C. The barb 38 may be disposed anywhere along the length of the elongated member 12C. The barb comprises a curved elastic member 22C embedded within a flexible material 24C. The barb 38 may or may not create an opening in the elongated member 12C depending on the depth of the cut made in the elongated member 12C. In the embodiment depicted in FIG. 6, the barbed portion 38 forms an opening 40.

To form the barbed retention structure 38 a piece of tubing is extruded to have a central lumen surrounded by a smaller outer lumen in a wall of the elongated member 12C. Two angled cuts are made into the wall of the elongated member 12C intersecting to form end 39. The end 39 of the barb extending laterally from the elongated member 12C exposes the small lumen. An elastic member 22C is shaped into a curved geometry that will form to the shape of the barb 38.

The curved length of elastic member is then inserted into the small lumen through end 39.

Referring to FIG. 9, insertion of the device 10C into a body of a patient can be accomplished by placing the device 10C in a conventional delivery system 41 and inserting the delivery system 41 into a body of a patient. In FIG. 9, the device 10C is disposed over a rigid member 43 on the delivery system 41. The delivery system 41 comprises a handle 45, a threaded hub 47, the rigid member 43, and an adapter 51 designed to attach the medical device 10C. When the device 10C is disposed over the rigid member 43, the end 37 of the barb 38 formed integrally with the elongated member 12C is preferably inserted into the body first so that the barb 38 folds into the opening 40 created in the elongated member 12C. For applications where end 39 of the barb is to be inserted first, a cannula 53 may be inserted over the elongated member 12C to cover and collapse the barb 38 therein. Once the device is positioned into the body, the cannula is withdrawn deploying the barb within a body cavity thereby anchoring the device 10C in the body.

FIG. 10 shows a reinforced inward spiral coil retention structure 42. The inward spiral retention structure may be disposed at either end or at both ends of the elongated member 12D. The elongated member 12D extends along a longitudinal axis 16D. The spiral coil 42 extends along a lateral axis 18D relative to the longitudinal axis 16D. The spiral coil 42 anchors the medical device 10D in place to prevent migration. As with the single and double retention coils (FIGS. 1 and 5), the elastic member 22D embedded within the flexible material 24D in the spiral coil retention structure 42 may be disposed along its inner perimeter. Alternatively, the elastic member may be disposed along the outer perimeter of the coil or along its flanks. It may optionally also extend within a portion of the elongated member 12D itself. The lumen 20D extends through at least a portion of the spiral coil 42 to facilitate drainage of fluid and other substances and may extend all the way through the spiral coil 42. The elongated member 12D and the retention structure 42 may incorporate a plurality of holes 30D and/or a large drain hole slot 28D to further facilitate drainage. Insertion of the device 10D into a body of a patient can be accomplished through use of the insertion catheter shown in FIG. 2.

To form a J curl retention structure, a single cut between approximately ⅜ and ¾ of a turn along the spiral coil retention structure may be made. As shown in FIG. 10, two examples of suitable cuts 55 and 56 made in the spiral coil retention structure at approximately ⅜ and ¾ of a turn respectively form the J curl retention structure. After the cut is made, the open end of the retention structure may then be tapered on both sides to form a small opening at the distal tip of the device.

To form the inward spiral retention structure, a dual lumen elongated member of flexible material is provided. An elastic member pre-formed into an inward coil may be inserted into one of the lumens, and the elongated member wound about itself to form the designated structure. Alternatively, the pre-formed elastic member 22 may be bound to an outer wall of the flexible material 24, and the distal end of the elongated member of flexible material wound about itself.

Figure 11:
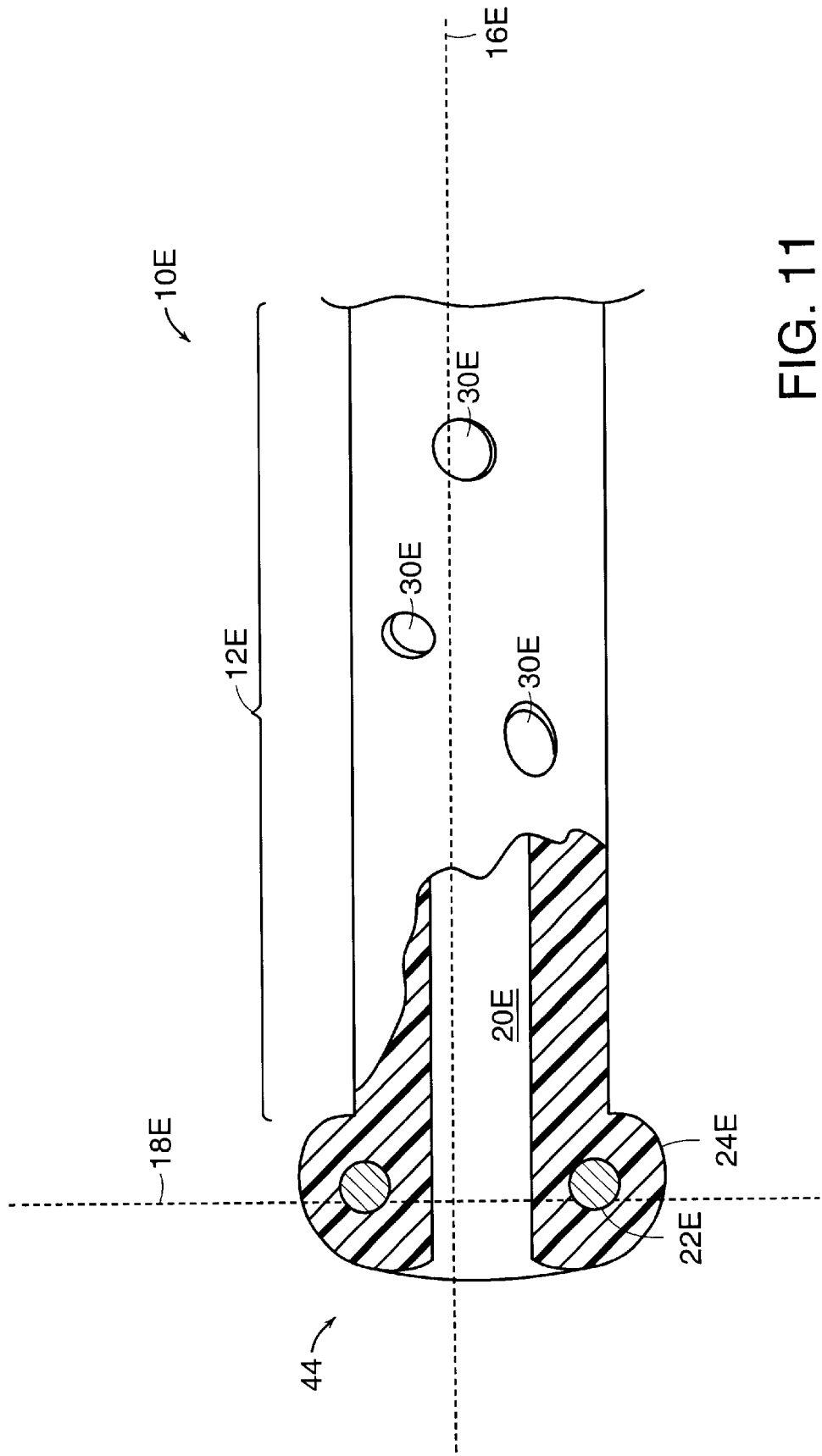
FIG. 11 is a schematic longitudinal view of a portion of an embodiment of the medical device of the invention with an elastic ring retention structure.

Referring to FIG. 11, a reinforced retention structure of the invention can be an elastic ring 44 containing an elastic member 22E embedded within a flexible material 24E. The elongated member 12E extends along a longitudinal axis 16E. The retention structure 44 extends along a lateral axis 18E relative to the longitudinal axis 16E. The reinforced ring may be at a 90° angle transverse from the longitudinal axis 16E or at a lesser angle designed to adapt to various internal body openings. The elastic ring or rings 44 protrude from the external surface of the elongated member 12E. The elastic rings 44 are designed to provide rigidity to the device and prevent migration of the device 10E. Drainage holes or apertures 30E are disposed along the length of the elongated member 12E to provide for fluid communication with the lumen 20E and to facilitate urinary drainage.

Figure 12A:
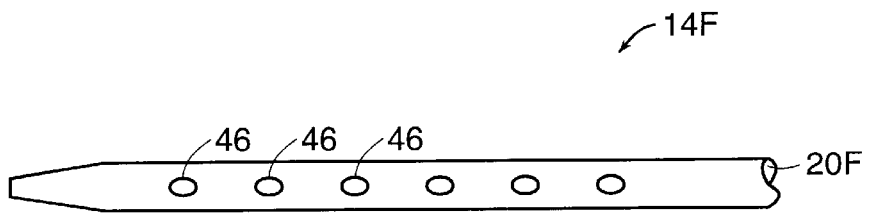
FIGS. 12A–B are schematic longitudinal views of a portion of two medical devices of the invention with collapsed retention structures illustrating a comparison of a series of holes configuration (FIG. 12A) with the reinforced large drain hole configuration of the present invention (FIG. 12B).
Figure 12B:
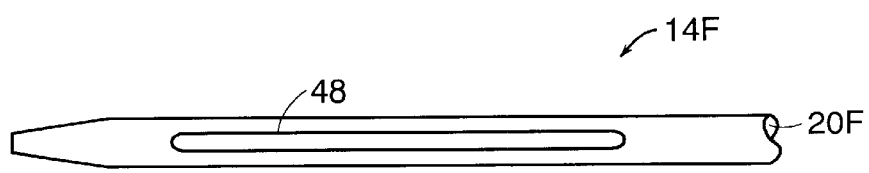

FIGS. 12A–B show retention structures of the present invention in a straightened configuration. In FIG. 12A, a plurality of holes 46 are cut into a retention structure to increase the drainage rate of fluid passing through the lumen 20F. In FIG. 12B, use of an elastic member provides stability to the retention structure 14F to support a large continuous drain hole slot 48 in the surface of the retention structure 14F. The drain hole slot 48 may also appear in the elongated member (not shown) if the elastic member extends out of the retention structure 14F into the elongated member. The length and width of the drain hole slot can vary depending on the needs of the particular patient. The width of the drain hole slot can be very narrow to prevent tissue in-growth.

Figure 13:
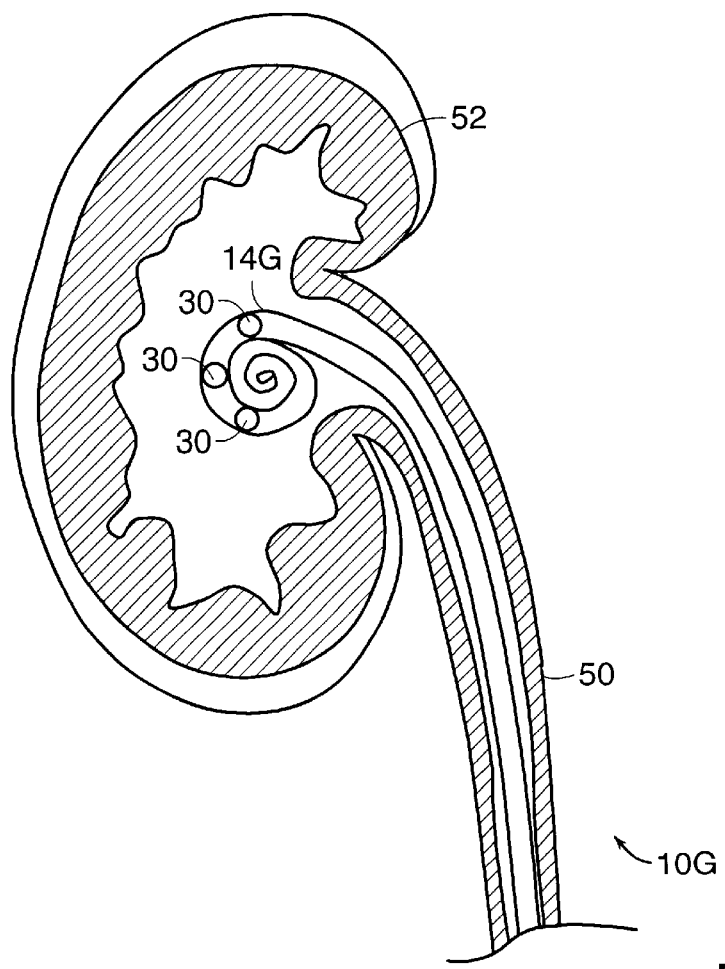
FIG. 13 is a schematic diagram illustrating the medical device of the invention implanted within the kidney and ureter of a patient.

One medical device of the present invention 10G placed into a body of a patient is illustrated in FIG. 13. The medical device 10G comprises an elongated member made of a flexible material and a reinforced retention structure 14G including an elastic member in the flexible material. The retention structure 14G featured in FIG. 13 has the geometry of an inward spiral coil, but other retention structures described above may also adequately be employed. The device 10G is easily inserted into the body through the ureter 50 and into the kidney 52 of the patient, as pictured herein. Insertion is accomplished in any conventional manner, such as collapsing the retention structure of the device 14G using a guidewire, stylet or cannula and then inserting the device 10G through the urethra. After insertion and removal of the straightening device, the retention structure 14G of the medical device reverts to a pre-determined geometry.

A method of manufacturing the medical devices of the present invention (FIGS. 1, 5, 6, 8, 10, 11) comprises providing an elongated member made of a flexible material and affixing a elastic member to the flexible material to form a reinforced retention structure. The elastic member is first shaped by mechanical operation at elevated temperatures, for example 500° C. The elastic member may be shaped into a curl, a coil, a malecot, a ring or a barb. Next, the elastic member may be positioned in the flexible material in a number of ways. For example, the pre-shaped elastic member may be introduced into a lumen of a multi-lumen extrusion tube of flexible material. The elastic member may be fed through one of the lumens of the multi-lumen extrusion by hand or by mechanical operation. The elastic member may also be molded in a thermosetting material, in that the pre-shaped elastic member is placed in a mold cavity and a flexible material poured around it such that it may ultimately bind to an external or internal surface of the flexible material. Also, the elastic member may be bound to an external or internal surface of the flexible material with glue or tape.

Variations, modifications, and other implementations of what is described herein will occur to those of ordinary skill in the art without departing from the spirit and scope of the invention. Accordingly, the invention is to be defined not only by the preceding illustrative description.

What is claimed is:

1. A medical device, comprising:
an elongated member comprising a flexible material and defining a lumen extending through the elongated member; and
a reinforced retention structure extending from the elongated member and comprising the flexible material and a superelastic member embedded in the flexible material, the reinforced retention structure for holding the device in place within the body of a patient.

2. The medical device of claim 1 wherein the reinforced retention structure comprises a curved segment of the elongated member, with the lumen of the elongated member extending through the curved segment, the curved segment being straightenable when a rigid member is inserted through the lumen.

3. The medical device of claim 2 wherein the curved segment comprises a curl.

4. The medical device of claim 2 wherein the curved segment comprises a coil.

5. The medical device of claim 1 wherein the reinforced retention structure comprises a collapsible ring, with the lumen of the elongated member extending through the ring, the ring being collapsible when an outer sheath is disposed over the device.

6. The medical device of claim 1 wherein the elongated member comprises a distal portion, a proximal portion and a middle portion and wherein the retention structure extends from at least one of the distal, middle and proximal portions.

7. The medical device of claim 1 further comprising a second reinforced retention structure.

8. The medical device of claim 1 wherein the reinforced retention structure defines at least one drain hole.

9. The medical device of claim 1 wherein the reinforced retention structure defines at least one drain hole slot.

10. The medical device of claim 1 wherein the superelastic member comprises nickel and titanium.

11. The medical device of claim 10 wherein the nickel comprises about 50% to about 52% by weight.

12. The medical device of claim 10 wherein the nickel comprises about 47% to about 49% by weight.

13. The medical device of claim 1 wherein the flexible material comprises plastic.

14. The medical device of claim 1 wherein the device is selected from the group consisting of a drainage catheter, a ureteral stent, a urethral stent, a biliary stent, and a prostatic stent.

15. The medical device of claim 1 wherein the superelastic member is a wire having a secondary two-dimensional structure disposed within a longitudinal plane.

16. The medical device of claim 15 wherein the superelastic member forms a J curl.

17. The medical device of claim 1 wherein the superelastic member is a wire having a secondary three-dimensional structure.

18. The medical device of claim 1 further comprising a second superelastic member within the elongated member.

19. The medical device of claim 18 wherein the second superelastic member is removable.

20. A medical device, comprising:
an elongated member comprising a flexible material and defining a lumen extending through the elongated member; and
a reinforced malecot retention structure comprising at least two arms, each of the arms comprising an elastic member and the flexible material and formed of the flexible material, the retention structure positioned along a portion of the length of the elongated member, the reinforced retention structure for holding the device in place within the body of a patient.

21. The medical device of claim 20 wherein the elongated member comprises a distal portion, a proximal portion and a middle portion and wherein the retention structure extends from at least one of the distal, middle and proximal portions.

22. The medical device of claim 20 further comprising a second reinforced retention structure.

23. The medical device of claim 20 wherein the reinforced retention structure defines at least one drain hole.

24. The medical device of claim 20 wherein the reinforced retention structure defines at least one drain hole slot.

25. The medical device of claim 20 wherein the elastic member is selected from the group consisting of a superelastic material, a polymeric material and stainless steel.

26. The medical device of claim 25 wherein the superelastic material comprises nickel and titanium.

27. The medical device of claim 26 wherein the nickel comprises about 47% to about 52% by weight.

28. The medical device of claim 20 wherein the device is selected from the group consisting of a drainage catheter, a ureteral stent, a urethral stent, a biliary stent, and a prostatic stent.

29. A medical device comprising:
an elongated member comprising a flexible material and defining a lumen extending through the elongated member;
and a reinforced barb retention structure comprising at least one barb extending from the flexible material of the elongated member, the at least one barb comprising an elastic member and the flexible material, the reinforced retention structure for holding the device in place within the body of a patient.

30. The medical device of claim 29 wherein the elongated member comprises a distal portion, a proximal portion and a middle portion and wherein the retention structure extends from at least one of the distal, middle and proximal portions.

31. The medical device of claim 29 further comprising a second reinforced retention structure.

32. The medical device of claim 29 wherein the reinforced retention structure defines at least one drain hole.

33. The medical device of claim 29 wherein the reinforced retention structure defines at least one drain hole slot.

34. The medical device of claim 29 wherein the elastic member is selected from the group consisting of a superelastic material, a polymeric material and stainless steel.

35. The medical device of claim 34 wherein the superelastic material comprises nickel and titanium.

36. The medical device of claim 35 wherein the nickel comprises about 47% to about 52% by weight.

37. The medical device of claim 29 wherein the device is selected from the group consisting of a drainage catheter, a ureteral stent, a urethral stent, a biliary stent, and a prostatic stent.

38. The medical device of claim 29 further comprising a second elastic member within the elongated member.

39. The medical device of claim 38 wherein the second elastic member is removable.

40. A medical device, comprising:
an elongated member comprising a flexible material and defining a lumen extending therethrough; and
a reinforced retention structure extending from the elongated member and comprising the flexible material and a superelastic member embedded in the flexible material, the reinforced retention structure for holding the device in place within the body of a patient.

41. The medical device of claim 40 wherein the reinforced retention structure comprises a curved segment of the elongated member, with the lumen of the elongated member extending through the curved segment, the curved segment being straightenable when a rigid member is inserted through the lumen.

42. The medical device of claim 41 wherein the curved segment comprises a curl.

43. The medical device of claim 41 wherein the curved segment comprises a coil.

44. The medical device of claim 40 wherein the reinforced retention structure comprises a collapsible ring, with the lumen of the elongated member extending through the ring, the ring being collapsible when an outer sheath is disposed over the device.

45. The medical device of claim 40 wherein the elongated member comprises a distal portion, a proximal portion and a middle portion and wherein the retention structure extends from at least one of the distal, middle and proximal portions.

46. The medical device of claim 40 further comprising a second reinforced retention structure.

47. The medical device of claim 40 wherein the reinforced retention structure defines at least one drain hole.

48. The medical device of claim 40 wherein the reinforced retention structure defines at least one drain hole slot.

49. The medical device of claim 40 wherein the elastic member is selected from the group consisting of a superelastic material, a polymeric material and stainless steel.

50. The medical device of claim 49 wherein the superelastic material comprises nickel and titanium.

51. The medical device of claim 50 wherein the nickel comprises about 50% to about 52% by weight.

52. The medical device of claim 50 wherein the nickel comprises about 47% to about 49% by weight.

53. The medical device of claim 40 wherein the flexible material comprises plastic.

54. The medical device of claim 40 wherein the device is selected from the group consisting of a drainage catheter, a ureteral stent, a urethral stent, a biliary stent, and a prostatic stent.

55. The medical device of claim 40 wherein the elastic member is a wire having a secondary two-dimensional structure disposed within a longitudinal plane.

56. The medical device of claim 55 wherein the elastic member material forms a J curl.

57. The medical device of claim 40, wherein the elastic member is a wire having a secondary three-dimensional structure.

58. The medical device of claim 40 further comprising a second elastic member within the elongated member.

59. The medical device of claim 58 wherein the second elastic member is removable.

60. A method of placing a medical device within a body of a patient, comprising:

provided a medical device comprising an elongated member comprising a flexible material defining a lumen extending through the elongated member and a reinforced retention structure extending from the elongated member, the reinforced retention structure the flexible material and a superelastic member embedded in the flexible material.

\* \* \* \* \*

UNITED STATES PATENT AND TRADEMARK OFFICE
CERTIFICATE OF CORRECTION

PATENT NO. : 6,569,150 B2 Page 1 of 1
DATED : May 27, 2003
INVENTOR(S) : Teague et al.

It is certified that error appears in the above-identified patent and that said Letters Patent is hereby corrected as shown below:

Column 14,
Line 28, after "the reinforced retention structure," insert -- comprising --.
Line 30, after "the flexible material," insert
-- the reinforced retention structure for holding the device in place within the body of the patient; and
inserting the medical device into the body of the patient --.

Signed and Sealed this

Thirteenth Day of April, 2004

JON W. DUDAS
*Acting Director of the United States Patent and Trademark Office*